(12) United States Patent
Greenstein et al.

(10) Patent No.: US 6,485,117 B1
(45) Date of Patent: Nov. 26, 2002

(54) DATA CARD DRAWER AND METHOD OF USE

(75) Inventors: Alan P Greenstein, Seattle, WA (US); Daniel J Powers, Issaquah, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/510,483

(22) Filed: Feb. 23, 2000

(51) Int. Cl.[7] ............................................. A47B 81/06
(52) U.S. Cl. .................... 312/9.43; 312/223.2; 312/9.47
(58) Field of Search ............................. 312/9.42, 9.53, 312/9.11, 223.2, 9.41, 9.47, 9.48, 9.56

(56) References Cited

U.S. PATENT DOCUMENTS

| 4,700,840 A | 10/1987 | Haddock |
| 4,763,962 A | * 8/1988 | Ackeret ............... 312/9.52 |
| 5,941,375 A | 8/1999 | Kamens et al. |

* cited by examiner

*Primary Examiner*—Peter M. Cuomo
*Assistant Examiner*—Jerry A. Anderson

(57) ABSTRACT

A data card drawer for installing a data card, such as a compact flash card, into a device that uses data cards. Devices that use data cards include, for example, medical devices, and more particularly defibrillators. The data card drawer electrically isolates the data card from the user when the user is installing or removing the data card from the device. The data card drawer may also be formed to provide a closure to the opening in the device housing provided to receive the data card. Further, the data card drawer may be formed to prevent damaging pins located on a pin connector within the receiving device which communicate data with the data card. The data card drawer preferably mates with the device to prevent ingress and egress of foreign matter and moisture.

11 Claims, 5 Drawing Sheets

DATA CARD DRAWER AND METHOD OF USE

BACKGROUND OF THE INVENTION

1. Field of the Invention

This invention relates to a data card drawer used to install a data card, such as a compact flash card, into a device that uses data cards. The data card drawer electrically isolates the data card from the user when the user is installing or removing the data card from the device. Further, the data card drawer prevents transfer of electrostatic discharge ("ESD") from the user to the device. The data card drawer may also be formed to provide a closure to the opening in the device housing provided to receive the data card. Further, the data card drawer may be formed to prevent damaging pins located on a pin connector within the receiving device which communicate data with the data card. The data card drawer preferably mates with the device to prevent ingress and egress of foreign matter and moisture.

2. Description of the Prior Art

Many electronic devices today use data cards, such as compact flash cards, (referred to as "cards") for data storage. In order to maximize data storage capability, cards are typically manufactured using a predominantly metal housing. The vast majority of cards having a two metal sides separated by a three-sided plastic frame. The internal circuitry resides within the housing formed by the metal sides and plastic frame. The remaining face of the card is filled with a 50-position pin connector (in a socket arrangement). The receiving device has a 50-pin connector. The 50-position pin connector of the card mates with a 50-pin connector in the receiving device in a pin-socket arrangement. Once mated, data exchange is possible between the card and the receiving device. An example of a compact flash card used for data is the Compact 2000 Flash Disk by M-Systems or any other standard compact flash card.

When installing the card, the user typically grasps the card directly by the card housing and inserts the card into a data slot on the receiving device. Receiving devices are any devices that are configured to receive data from or store data on a card.

One such receiving device that utilizes cards is the Hewlett-Packard 620LX palmtop. The 620LX uses cards for data storage. A data card drawer is used to install and remove the data card from the 620LX. However, the data card drawer does not provide a user-device isolation function since, although the front of the drawer is hard plastic, the drawer body is metal. The use model of the 620LX is such that user isolation from the card during the installation and removal is not essential. Therefore, using a data card drawer with a metal body does not present a risk to the user from handling the card during installation and removal.

Survivalink uses a compact flash card in its defibrillator. Electrical isolation of the card from the user is enabled by manufacturing the data card with an all-plastic housing. The absence of any external metal allows the user to grasp the card directly without compromising user isolation. There are several drawbacks to this solution. First, all-plastic housings are supplied in very small quantities and by very few vendors. Further, because the all plastic housing is thicker, there is less usable space for data inside the card. This limits the card design to single-sided circuit boards and, hence, provides less memory. This design also requires the use of a special off-center connector in the card because of the single-sided circuit board. Because of these constraints, all-plastic cards are difficult to procure and significantly more expensive than the standard metal-sided variety with the added detraction of providing less memory.

Electrical isolation of the user from the device can be extremely important in some use models, such as when the card is used in a medical device, particularly where high voltages are present, or when there is a risk of damaging the device due to ESD transfer from the user to the device. Additionally, the ability to prevent damage to the installed card under mechanical impact. Finally, the ability to install the card in such a way as to prevent ingress of environmental residue is also important. What is needed, therefore, is an apparatus that electrically isolates the user from the device while the card is being installed such that a user is prevented from being simultaneously in electrical contact with the card while installing the card into a device. Further what is needed is an apparatus that prevents damage to the flash card connector mechanism when the installed card is subjected to mechanical force. Finally what is needed is an apparatus that installs the card into the receiving device while providing a mechanism to prevent ingress of environmental residue into the device.

SUMMARY OF THE INVENTION

A data card holder for installing a data card into a receiving device comprising: a housing having an interior portion formed from a bottom wall, a front wall and two side walls; a keying detent located on at least one side wall of the housing wherein the detent protrudes into the interior of the housing; and a handle formed on the front wall of the housing wherein the handle is formed on a face of the front wall that is exterior to the interior of the housing. In this data card holder, the interior portion of the housing further has a flange attached to the front wall and parallel to the bottom wall of the housing. The bottom wall of the housing may further have a cut-out portion. The front wall of the housing may further comprise a second keying detent. Along the front wall of the housing the data card holder may further comprise a safety rib along the front wall protruding into the interior of the housing. The front wall of the housing may also have a sealing rib around its perimeter.

In another embodiment, a data card holder for installing a data card into a receiving device comprising: a housing having an interior portion formed from a bottom wall, a front wall and two side walls; a safety rib located on the front wall of the housing wherein the safety rib protrudes into the interior of the housing; and a handle formed on the front wall of the housing wherein the handle is formed on a face of the front wall that is exterior to the housing. The interior portion of the housing may further have a flange attached to the front wall and parallel to the bottom wall of the housing. Again, the bottom wall of the housing may further have a cut-out portion. In this embodiment, the data card holder may also have at least one side wall of the housing further comprises at least one detent. Optionally, the front wall of the housing has a sealing rib around its perimeter.

A method of isolating a user from a device when installing a data card is also contemplated. The method comprises: installing a data card having a metal housing in a data card holder formed of a non-conductive material; and installing the data card holder into a receiving device. The installing step of the method may also comprise: installing the data card into the data card holder so that notches on either side of the data card mate with a detent located on at least one side of the data card drawer.

It is also contemplated that this invention includes a method for preventing damage to a pin-connector in a receiving device when installing a data card drawer. This method comprises: installing a data card in a data card holder so that the data card fits snugly against a front wall portion of the data card holder; and installing the data card holder into a receiving device so that a detent located on the front wall portion of the data card holder abuts against a portion of the receiving device to prevent further entry.

Another method contemplated, includes the ability to install a data card into a high energy device. The steps of the method comprise: installing a data card having a metal housing in a data card holder formed of a non-conductive material; and installing the data card holder into the high energy device, wherein the user is electrically isolated from the high energy device while installing the data card holder into the device.

A further method of isolating a device from electrostatic discharge when installing a data card is also included. This method comprises: installing a data card having a metal housing in a data card holder formed of a non-conductive material; and installing the data card holder into a receiving device. Additionally, the installing step may further comprise: installing the data card into the data card holder so that notches on either side of the data card mate with a detent located on at least one side of the data card drawer.

Yet another method is contemplated. Specifically, the method of sealing an opening in a device for receiving a data card from ingress or egress of environmental material. The steps of this method comprise: installing a data card in a data card holder having a face; and installing the data card holder into a receiving device such that a rib on a perimeter of the face of the data card holder sealingly mates with the device for receiving the data card.

DESCRIPTION OF THE PREFERRED EMBODIMENTS

The following discussion is presented to enable a person skilled in the art to make and use the invention. Various modifications to the preferred embodiment will be readily apparent to those skilled in the art, and the generic principles herein may be applied to other embodiments and applications without departing from the spirit and scope of the present invention as defined by the appended claims. Thus, the present invention is not intended to be limited to the embodiment show, but is to be accorded the widest scope consistent with the principles and features disclosed herein.

Figure 1A:
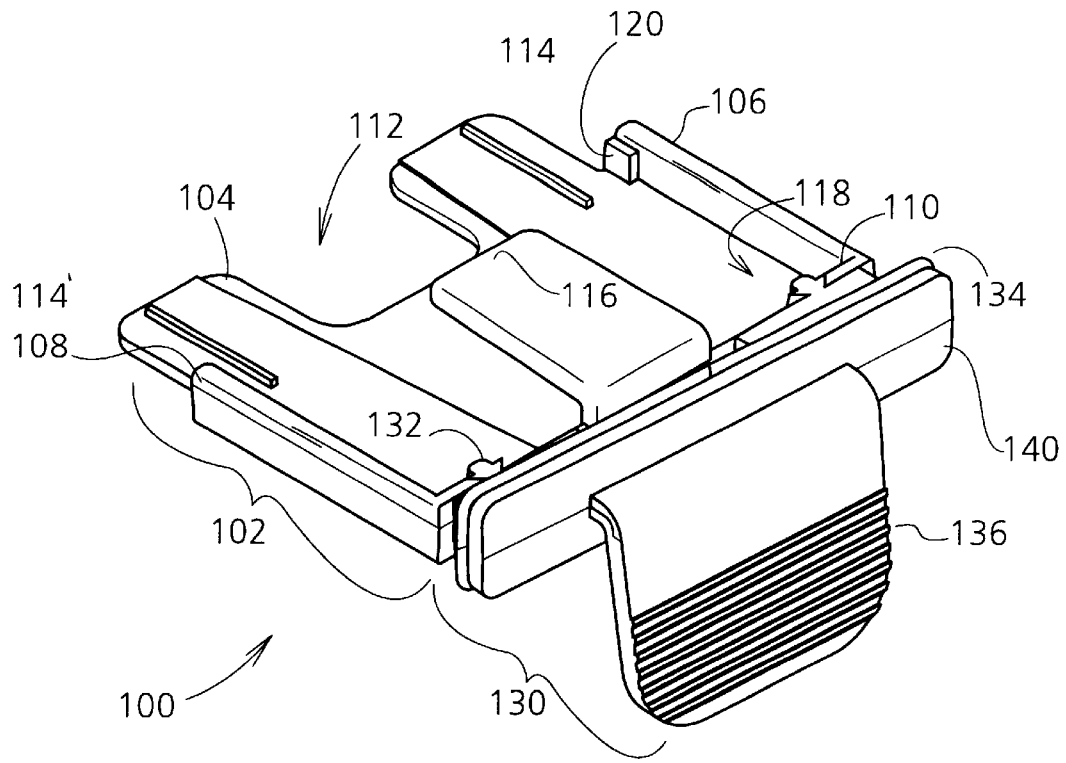
FIG 1a is a top perspective view of a data card drawer illustrating the elastomeric sealing feature and the tongue handle located on the front portion of the drawer.

FIG. 1a is a top perspective view of the data card drawer assembly 100. The main housing portion of the drawer 102 has a bottom 104, a right side 106, a left side 108 and a front side 110. The main portion of the housing 102 is formed from a rigid plastic material such as a polycarbonate. Other suitable materials would be apparent to one of skill in the art. Suitable materials would have, for example, a modulus of elasticity in the range of 250,000 to 400,000 psi, most preferably 350,000 psi.

The bottom 104 portion of the housing has a cut-away section 112 to enable the user to grasp the card when it is installed. In this embodiment, the cut-away section 112 is essentially rectangularly dimensioned. Two ridges 114, 114' are located on the rectangular portions of the bottom section that flank the cut-away section 112. The two ridges 114, 114' are provided to orient the installed card 200 (shown in FIG. 2) in a way that enables the card 200 to mate securely with a pin connector located within the housing of the receiving device (shown in FIG. 3). A flange 116 is provided along the top to secure the installed data card within the data card drawer 100.

A pair of keying detents 120, 120' are provided on the right 106 and left 108 side of the main portion of the housing. The keying detents 120, 120' provide two functions. First, the keying detents 120, 120' keep the data card 200 within the data card drawer 100 during installation and removal of the data card from the receiving device. Keying detents 120, 120' are formed to fit within a notch located on either side of the card. Further keying detents 120, 120' act as a key feature because the detents prevent the data card from being installed into the data card drawer 100 incorrectly (e.g. in an upside-down orientation). As will be appreciated by a person of skill in the art, the number and orientation of the keying detents can be changed as appropriate for the design of the card. Such an alteration is within the scope of the invention.

The front side of the housing has two openings 118, 118' which are used to facillitate mating with a front panel section.

As shown, a front panel section 130 is formed to mate integrally with the main housing portion of the drawer 102. In this embodiment, the front panel section 130 is formed from a non-conductive elastomeric substance. Suitable elastomeric substances, include, for example, Pellethane® (manufactured by Dow-DuPont) having an elasticity between 70 and 90 durometers on the Shore A scale. Alternatively, the front panel section 130 may be formed integrally with the main housing portion of the drawer 102. Where the front panel section is formed integrally with the main housing portion of the drawer 102, either an elastomeric substance could be used or the front panel could be formed from the same material as the main housing portion of the drawer 102. However, in the event that the front panel is manufactured from the same material as the main housing, the ability to form a suitable seal may be compromised.

Figure 7:
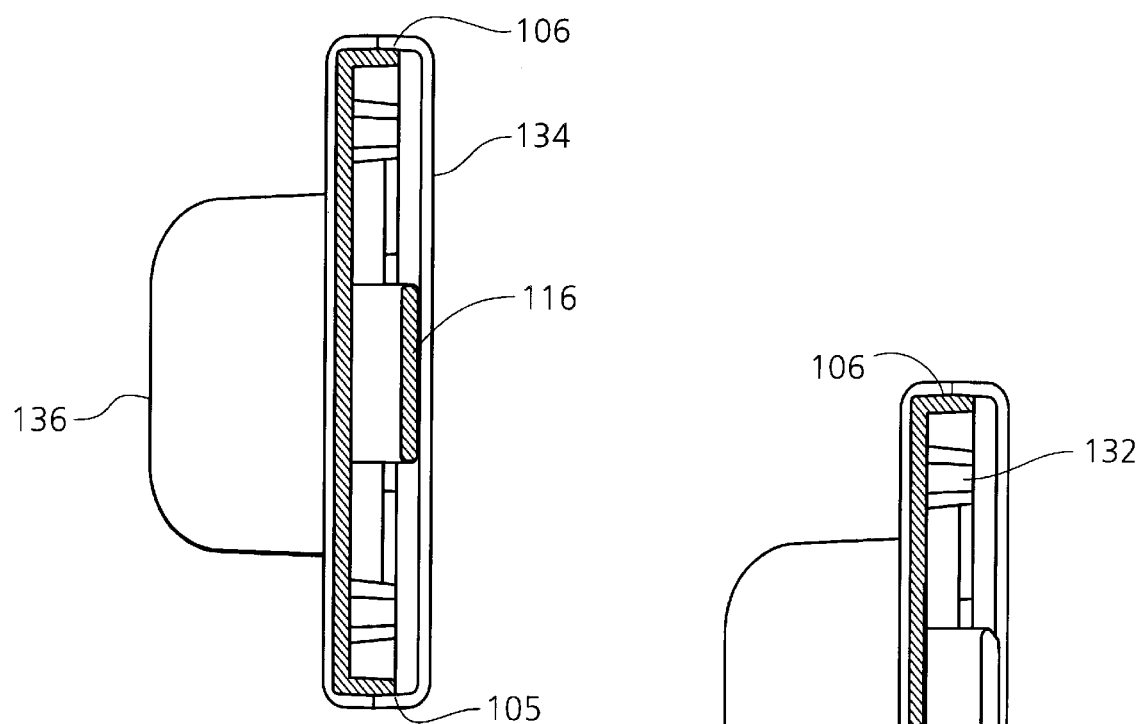
FIG. 7 is a transverse-sectional view along the lines 7—7 shown in FIG. 2.

The front panel portion has a main facing section 140 with two safety ribs 132, 132' formed as part of the front panel section 130 that extend through the openings 118, 118' of the front section of the main portion of the housing (shown in more detail in the cross-section view of FIG. 7). The safety ribs 132, 132' provide a flexible surface for the card to engage when the card is being installed in the receiving device 300. Further the top portion of the safety ribs 132, 132' mate against a portion of the receiving device interior such as the printed circuit board housed within the receiving device. Thus, if the device were dropped on the surface containing the data card drawer, the mechanical impact would not force the data card drawer 100 into the housing. This results because the safety ribs 132, 132' abut a portion of the receiving device interior thus preventing the card drawer from further entry into the device interior. By preventing the data card drawer 100 from being forced into the receiving device opening, the safety ribs 132, 132' reduce the likelihood that the pin-connector located within the receiving device will be damaged. As will be appreciated by a person of skill in the art, the number and orientation of the safety ribs 132, 132' can be modified without departing from the spirit of the invention.

A sealing rib 134 is formed along the front panel section 130. The sealing rib 134 enables the front panel to seal the front portion of the front panel section 130 to the receiving device 300. Thus, when the data card drawer 100 is installed, and the seal is formed, ingress of environmental materials is prevented. A tongue or handle 136 is further provided in the front panel section 130. The tongue 136 provides the user with a convenient way to install and remove the data card drawer assembly 100 from the receiving device.

As illustrated in FIG. 1a, the front panel section 130 is formed at an angle with the main housing portion 102. This orientation is employed in this example to enable the perimeter edges of the data card drawer assembly 100 to match the profile of the housing of the receiving device when installed. As will be appreciated by those of skill in the art, this off-set orientation is not necessary to practice the invention and is provided as an illustration only of a particular embodiment.

Figure 2:
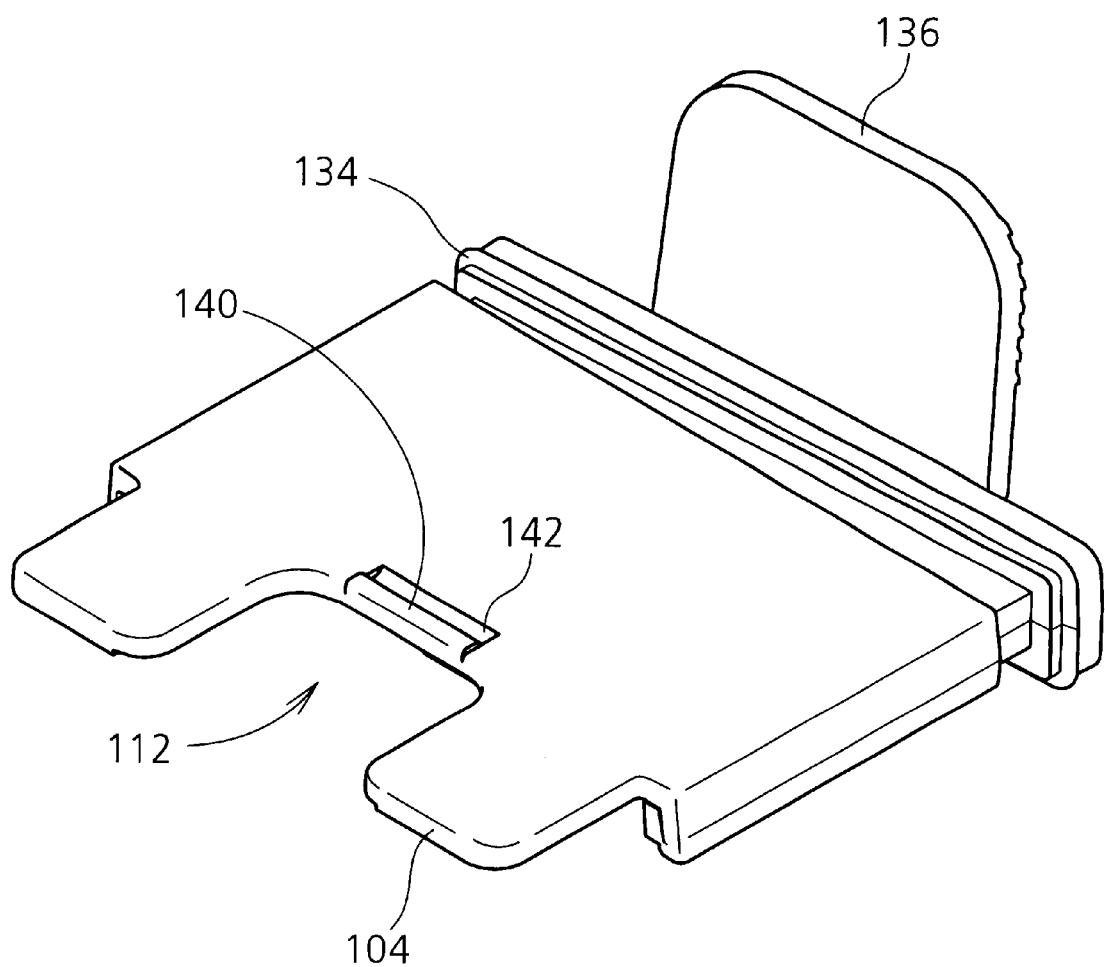
FIG. 2 is bottom perspective view of the data card drawer.

FIG. 2 illustrates a bottom perspective view of the data card drawer described in connection with FIG. 1a. A ridge 140 and channel 142 is provided in the bottom surface of the main housing portion 102 adjacent to cut-away section 112 to enable the data card drawer assembly to latch upon installation in the receiving device. An advantage of this feature is that it provides tactile feedback to the user that the installation of the data card assembly 100 is complete.

Figure 3A:
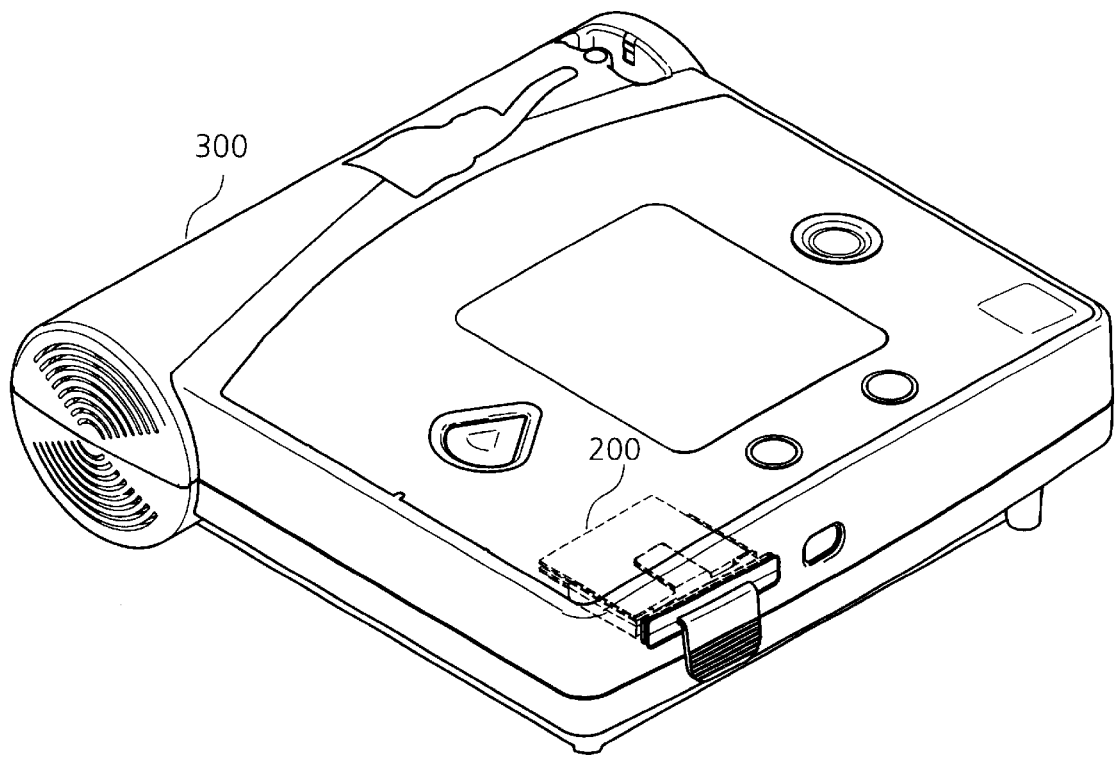
FIG. 3a is a top perspective view of the data card drawer with the compact flash card installed shown in the receiving device. Cut away lines are provided showing the bottom portions of the data card drawer and the mating of the keying detents within the notches in the data card.
Figure 3B:
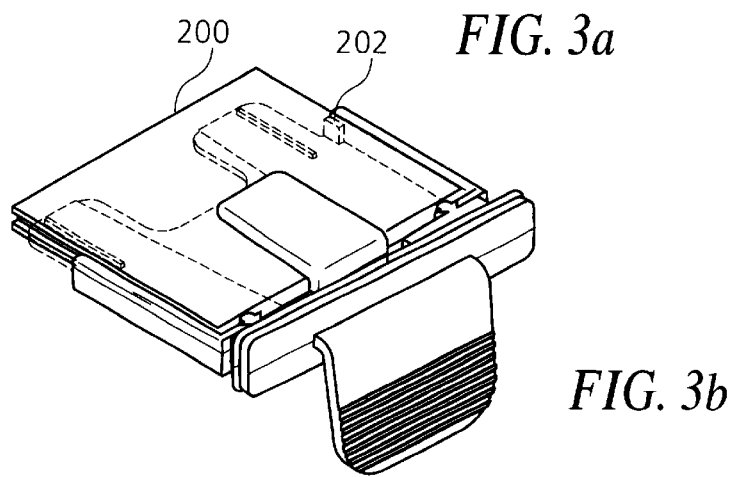
FIG. 3b is a top perspective view of the compact flash card installed in the data card drawer.

FIG. 3a illustrates a data card drawer assembly 100 with a data card 200 installed and the assembly installed in a receiving device 300. FIG. 3b illustrates the data card 200 installed in the data card drawer assembly 100. As evidenced from the cut away lines shown in FIG. 3b, the keying detents 120, 120' mate with the notch 202 located on either side of the data card 200. Further the face of the front portion of the data card assembly is oriented to mate with the face of the receiving device. The sealing rib 134 provides a sealing mechanism with the housing of the receiving device 300.

Figure 1B:
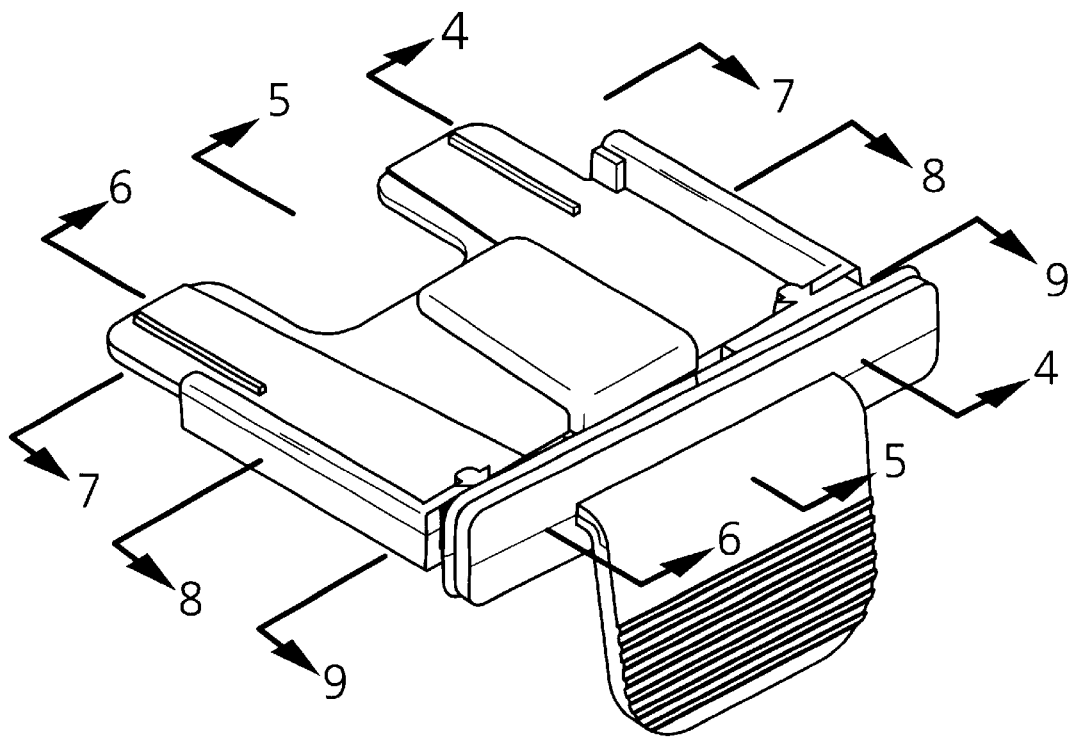
FIG. 1b is a top perspective view of the data card drawer indicating the transverse sections of FIGS. 4–9.
Figure 4:
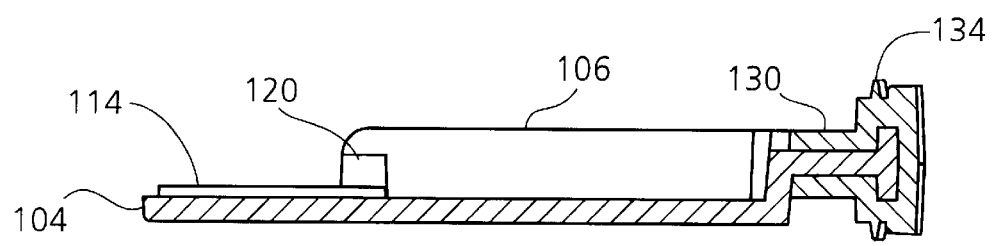
FIG. 4 is a transverse-sectional view along the lines 4—4 shown in FIG. 2.
Figure 5:
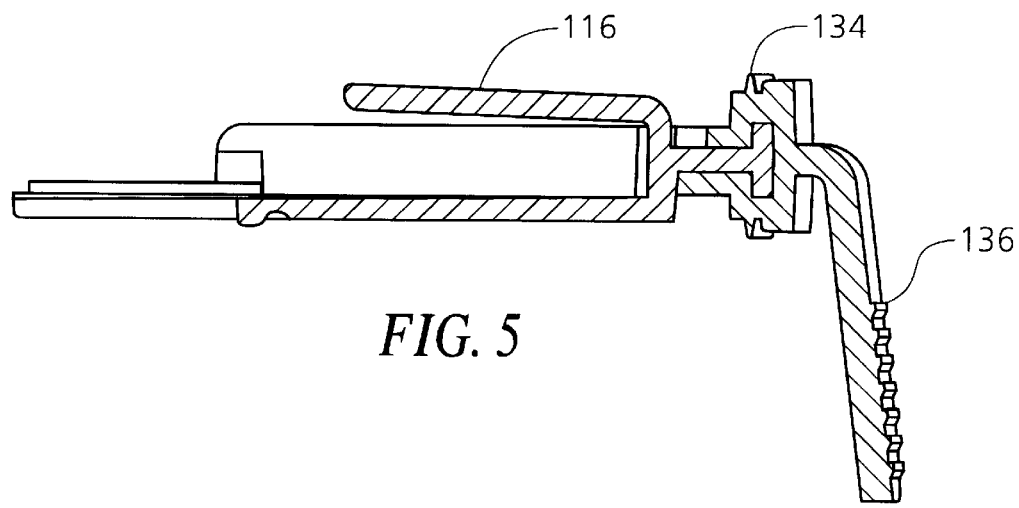
FIG. 5 is a transverse-sectional view along the lines 5—5 shown in FIG. 2.
Figure 6:
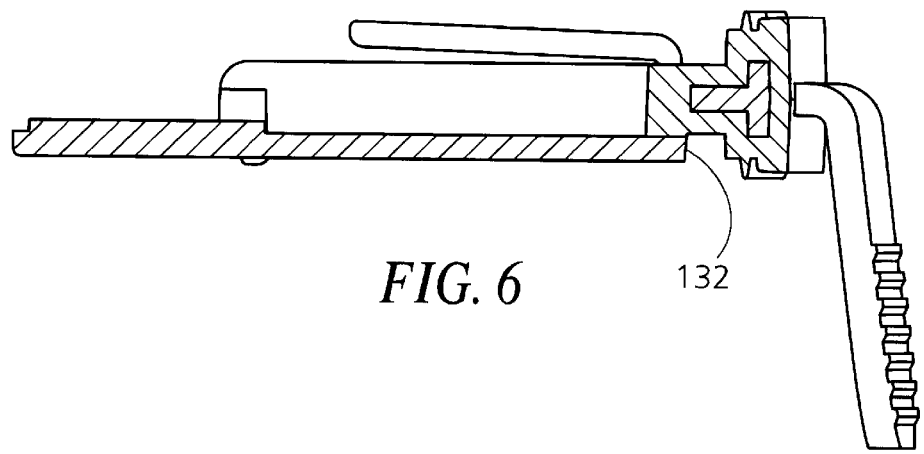
FIG. 6 is a transverse-sectional view along the lines 6—6 shown in FIG. 2.

FIGS. 4, 5 and 6 illustrate cross-sectional views of the data card drawer assembly along the lines 4—4, 5—5 and 6—6, respectively, shown in FIG. 1b. The cross-section shown in FIG. 4 cuts across the bottom 104 of the main housing portion of the drawer 102 and the front panel section 130. As illustrated by the cross-hatching of the two sections, the bottom section 104 and the front panel section 130 are formed integrally from different materials. As will be appreciated by a person of skill in the art, this dual material configuration is not required to practice the invention. In the background is the right side 106 of the main housing portion of the drawer 102 with one of the keying detents 120.

FIG. 5 illustrates a cross-sectional view of the data card along the lines 5—5. The cross-section at 5—5 cuts across a shortened portion of the bottom 104 of the main housing portion of the drawer 102 and the flange 116. As will be apparent, the shortened portion of the bottom 104 is a result of cut-away section 112 shown in FIG. 1b. With respect to the main facing section 130, the cross-section cuts through the face 138, the ridge 140, and the handle 136.

The cross-section shown in FIG. 6 taken along the lines 6—6 cuts through the bottom 104 of the main housing portion of the drawer 102. Importantly, the cross-section cuts through at the location where the safety rib 132' protrudes through the opening 118 in the front side 110 of the main housing portion 102.

Figure 8:
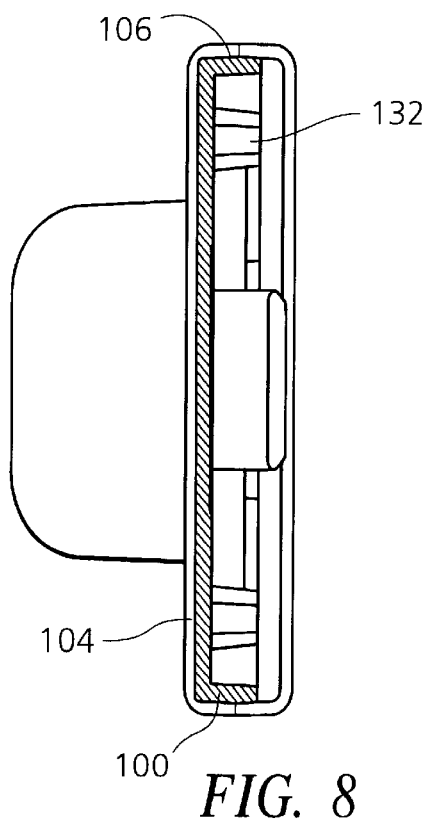
FIG. 8 is a transverse-sectional view along the lines 8—8 shown in FIG. 2.
Figure 9:
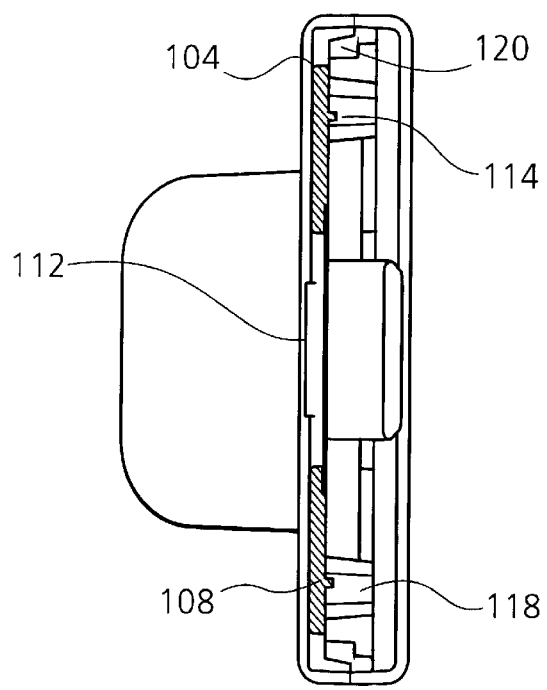
FIG. 9 is a transverse-sectional view along the lines 9—9 shown in FIG. 2.

FIGS. 7, 8 and 9 illustrate cross-sectional views of the data card drawer along the lines, 7—7, 8—8 and 9—9, respectively, also shown in FIG. 1b. Lines 7—7, 8—8 and 9—9 are taken perpendicular to the views shown in FIGS. 4–6.

The cross-section at 7—7 shown in FIG. 7 cuts through the bottom portion that partially defines the cut-out portion 112 shown in FIG. 1b. The cross-section at 8—8 shown in FIG. 8 cuts through the entire main housing portion of the drawer 102, including the right side 106, the left side 108 and the bottom 104. Turning to the cross-section at 9—9 shown in FIG. 9, the cross-section again cuts through the entire main housing portion of the drawer 102 as well as the flange 116.

Turning now to the use of the data card drawer 100, a card 200 is inserted into the drawer assembly 100. In inserting the card 200, the card 200 is inserted at an angle such that the top face of the card is located below the flange 116 of the data card drawer and the bottom face of the card contacts the keying detents 120, 120'. In this orientation, the card 200 slides into the data card drawer 100 until the back portion of the card 200 meets with the safety ribs 132, 132' located at the front of the data card drawer. At that point, the notches 202 located on the side of the card are aligned with the keying detents 132, 132' and the card 200 is snapped into place within the data card drawer assembly 100. If the card 200 had been inserted in an upside-down or backward orientation, the card 200 would not snap into its final position since the notches 202, 202' and the keying detents 120, 120' would not align in such a way as to enable final positioning of the card 200.

Once the card 200 is completely installed in the drawer assembly 100, the data card drawer assembly 100 is then installed into the receiving device 300 such that the card 200 mates with the pin-connector within the receiving device 300. In installing the data card drawer assembly 100, the assembly is pushed into the receptacle for receiving the data card drawer until the safety ribs 132, 132' abut a portion of the device that prevents further insertion. At this same point, a snug mating is confirmed tactilely to the user when the notch 140 and channel 142 on the underside of the data card drawer 100 clicks into place within the device. The rib 134 of the data card drawer assembly 100 seals with housing of the receiving device 100 to prevent ingress of environmental materials.

In should be noted that a data card need not be installed in the data card drawer in order to effectively insert the data card drawer and effectuate a proper seal.

To remove the data card drawer assembly 100, including the card, the user pulls on the tongue 136 located on the face 140 of the data card drawer assembly 100. Pulling on the tongue 136 disengages the card 200 from the pin-connector within the device 300 and breaks the seal formed at the rib 134 between the data card drawer assembly 100 and the face of the device 300.

What is claimed:

1. A data card holder for installing a data card into a receiving device comprising:
    a housing having an interior portion formed from a bottom wall, a front wall and two side walls;
    a keying detent located on at least one side wall of the housing wherein the detent protrudes into the interior of the housing and is operable to engage a notch on a data card inserted into the data card holder;
    a handle formed on the front wall of the housing wherein the handle is formed on a face of the front wall that is exterior to the interior of the housing.

2. The data card holder of claim 1 wherein the interior portion of the housing further has a flange attached to the front wall and parallel to the bottom wall of the housing.

3. The data card holder of claim 1 wherein the bottom wall further has a cut-out portion.

4. The data card holder of claim 1 wherein the front wall further comprises a second keying detent.

5. The data card holder of claim 1 further comprising a safety rib along the front wall protruding into the interior of the housing.

6. The data card holder of claim 1 wherein the front wall of the housing has a sealing rib around its perimeter.

7. A data card holder for installing a data card into a receiving device comprising:
    a housing having an interior portion formed from a bottom wall, a front wall and two side walls;
    a safety rib located on the front wall of the housing wherein the safety rib protrudes into the interior of the housing and is operable to engage a data card inserted into the data card holder and to engage a portion of the receiving device to prevent overinsertion of the data card holder into the receiving device;
    a handle formed on the front wall of the housing wherein the handle is formed on a face of the front wall that is exterior to the housing.

8. The data card holder of claim 7 wherein the interior portion of the housing further has a flange attached to the front wall and parallel to the bottom wall of the housing.

9. The data card holder of claim 7 wherein the bottom wall of the housing further has a cut-out portion.

10. The data card holder of claim 7 wherein at least one side wall of the housing further comprises at least one detent.

11. The data card holder of claim 7 wherein the front wall of the housing has a sealing rib around its perimeter.

* * * * *